(12) United States Patent
Galle

(10) Patent No.: US 8,797,539 B2
(45) Date of Patent: Aug. 5, 2014

(54) SYSTEM AND METHOD FOR A VIRTUAL REFERENCE INTERFEROMETER

(76) Inventor: Michael Galle, Grimsby (CA)

( * ) Notice: Subject to any disclaimer, the term of this patent is extended or adjusted under 35 U.S.C. 154(b) by 402 days.

(21) Appl. No.: 13/203,186

(22) PCT Filed: Feb. 24, 2010

(86) PCT No.: PCT/CA2010/000246
§ 371 (c)(1),
(2), (4) Date: Oct. 3, 2011

(87) PCT Pub. No.: WO2010/096912
PCT Pub. Date: Sep. 2, 2010

(65) Prior Publication Data
US 2012/0013908 A1    Jan. 19, 2012

Related U.S. Application Data

(60) Provisional application No. 61/202,379, filed on Feb. 24, 2009, provisional application No. 61/221,905, filed on Jun. 30, 2009.

(51) Int. Cl.
*G01B 9/02* (2006.01)
(52) U.S. Cl.
USPC ............................................. 356/477
(58) Field of Classification Search
USPC .......................... 356/450, 477, 480
See application file for complete search history.

(56) References Cited

U.S. PATENT DOCUMENTS

| 4,955,719 A | 9/1990 | Hayes |
| 5,398,113 A | 3/1995 | De Groot |
| 2003/0103212 A1 | 6/2003 | Westphal et al. |
| 2007/0165238 A1* | 7/2007 | Boyd ............................. 356/478 |
| 2008/0204759 A1* | 8/2008 | Choi ............................. 356/482 |
| 2009/0097036 A1 | 4/2009 | Galle et al. |

FOREIGN PATENT DOCUMENTS

| WO | 2008091286 | 7/2008 |
| WO | 2009049393 | 4/2009 |
| WO | 2010096912 | 9/2010 |

OTHER PUBLICATIONS

International Search Report of the Authorized Searching Authority (corresponding to Application: PCT/CA2010/000246); Canadian Intellectual Property Office; Issued Jun. 16, 2010; (2 pages).
Written Opinion from the Authorized Searching Authority (corresponding to Application: PCT/CA2010/000246); Canadian Intellectual Property Office; Issued Jun. 6, 2010; (6 pages).

* cited by examiner

*Primary Examiner* — Jonathan Hansen

(57) ABSTRACT

An interferometer generates interference between two (or more) waves that have traveled separate paths so as to measure a quantity of difference between these paths. One of these paths, the reference path, is usually one with well known spatial and material properties (such as free 5 space). The other path(s) is(are) the test path(s). The main difficulties in interferometry stem from the production and operation of this physical reference path. The present invention solves this problem by replacing the physical reference path with a virtual one. This is done by suitable operation on the physically generated interference pattern of an unreferenced interferometer with a virtually generated sinusoid of frequency corresponding to the desired reference path length. The result is a new form of interferometer called a Virtual Reference Interferometer.

8 Claims, 8 Drawing Sheets

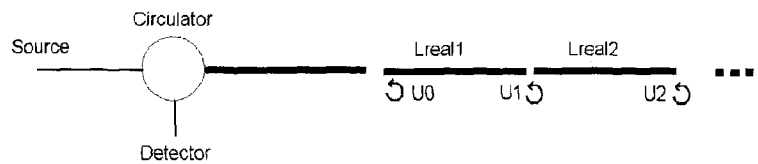
FIG. 8.
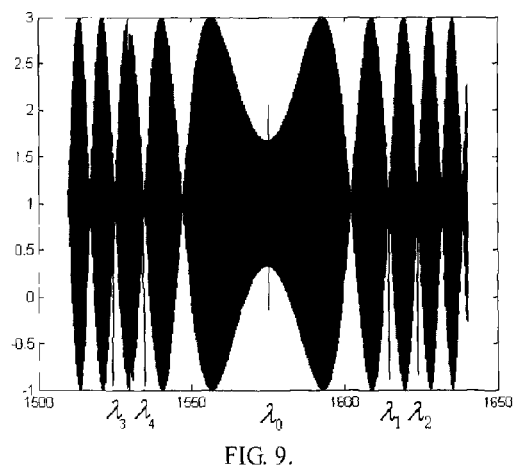
FIG. 9.
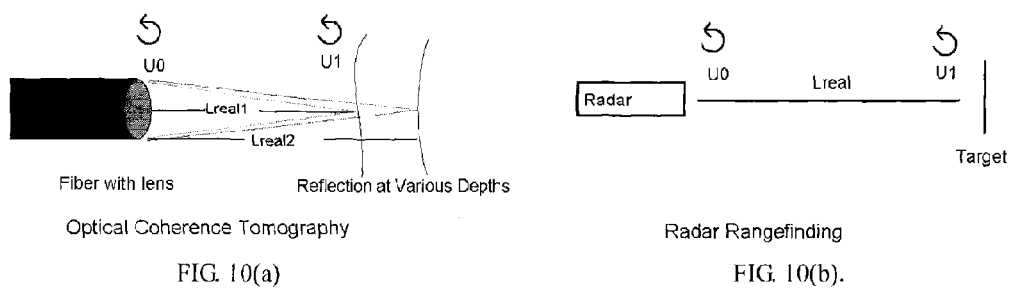
Optical Coherence Tomography
FIG. 10(a)
Radar Rangefinding
FIG. 10(b).

Focussed sound emission    Reflection at various depths

Ultrasound / Sonography

Sonar / Rangefinding

SYSTEM AND METHOD FOR A VIRTUAL REFERENCE INTERFEROMETER

PRIORITY CLAIMED

This application claims the benefit of U.S. Provisional Patent Application No. 61/202,379 filed Feb. 24, 2009 and U.S. Provisional Patent Application No. 61/221,905 filed Jun. 30, 2009.

FIELD OF THE INVENTION

The present invention relates generally to interferometry. The present invention relates more specifically to an interferometer that comprises a physical test component and a virtual reference component.

BACKGROUND OF THE INVENTION

Interference is the phenomenon whereby the wave vectors (amplitude and phase) of two or more waves (i.e. electromagnetic waves, sound waves etc.) are combined as they propagate along a common path. An interferometer is a device that generates this interference between two (or more) waves. The waves are first separated into two (or more) paths in order to measure a quantity that differentiates these paths (i.e. spatial or material differences). A phase difference between the waves in each path results from these differences. When the waves are recombined, the interference pattern can be used to measure this phase difference and provide information about the spatial and material differences between the paths. One of these paths is called the reference path and the other(s) is(are) the test path(s). The reference path is usually one that has well known spatial and material properties such as free space (vacuum) or air. The problem with interferometers today is that they all suffer from issues related the production and use of this physical reference arm.

Interferometers require one test arm (at least) and a reference arm. The reference arm is a physical path with well known characteristics. The most common reference arm is one that contains a variable free space path (such as a variable delay line—VDL) that can be used to change the length of the reference arm and/or balance the two arms of the interferometer.

Several possible implementations of physically balanced interferometers are given in FIG. 1. The examples shown are the Michelson Interferometer, the Single Arm Interferometer and the Mach Zehnder Interferometer. Fiber based (optical) implementations are shown but a similar diagram can be made for free space architectures or architectures that do not involve optical waves (i.e. sound waves). Note that the source can be any wave generating source such as, for example an RF source, microwave source, laser source, broadband source, X-ray source, sound wave generator etc. The detector/receiver can be any wave receiver such as for example an RF receiver, microwave receiver, laser detector, broadband receiver (optical spectrum analyser, monochromater or even a basic tuneable filter), X-ray detector, sound wave receiver. The discussion that follows assumes the use of a tunable laser as the source and a laser detector as the receiver. The choice of this pair for the source and detector is only to simplify the discussion and illustrate tangibly the issues related to using a physical reference and are not meant to limit the generality of the discussion.

An interferometer is balanced when the delay experienced by the wave traversing the reference arm is the same as the delay experienced by the wave traversing the test arm. When an interferometer is brought into balance the resulting interference pattern depends on the type of interferometer and the number of interfering waves. Various types of interferometers are shown in FIG. 1 and will be used in the discussion to follow.

Note that the following discussions involve the use of spectral interferometry which uses a tunable wavelength source and a detector to produce interference patterns with the wavelength as the dependent variable (can also be done spectrally using a broadband source and an optical spectrum analyzer—or any device that can discriminate between power levels at different wavelengths). This is not meant to limit the generality of this technology to spectrally acquired interference patterns. Interference patterns can also be produced by exploiting the temporal or spatial coherence of two waves. This can be done, for example, by using a broadband source, detector and a movable mirror. In this case, instead of using a laser that tunes (moves) its wavelength a mirror is moved so that the interference pattern produced is a function of the position of the movable mirror (located in the test path of an unbalanced interferometer). This type of Interferometry is temporal Interferometry. An application of this type of Interferometry is Fourier Transform Spectroscopy.

Dual Arm Interferometer

Several types of interferometers exist. The most common are interferometers with two (dual) arms. Some examples of dual arm interferometers are the Michelson Interferometer and the Mach Zehnder Interferometer (shown in FIG. 1). In a dual arm interferometer there are two interfering waves (U0 and U1). Let us take the Michelson interferometer as an example. The interfering waves in the Michelson interferometer can be described in the following way:

$$U0 = Ae^{(-2j\beta L_1)}$$

$$U1 = Ae^{(-2jk_o L_2)}$$

It has been assumed, for simplicity in this example, that the amplitudes of the reflected waves are equal (given by 'A') and that the simulated reference path is free space (given by the propagation constant $k_o$). Additionally, in this example, a general propagation constant, $\beta$, has been assumed for the test path. The interference pattern produced by the interference of U0 and U1 can be described as the square of the magnitude of the two interacting waves:

$$I = [U0 + U1]^2 = A^2(2 + 2\cos(2(\beta L_1 - k_o L_2)))$$

This interference pattern is shown in FIG. 2(a). From this we can see that the phase of the interference pattern is related to the difference between the two paths.

$$\phi = 2(\beta L_1 - k_o L_2)$$

The phase, therefore, can be used to obtain information about the test arm (described by $\beta L_1$) based on the knowledge of the reference arm (described by $k_o L_2$). Note that ko is the free space propagation constant ($k_o = 2\pi/\lambda$) where $\lambda$ is the wavelength. $L_1$ is the length of the test arm and $L_2$ is the length of the reference arm.

Single Arm Interferometer

In a Single Arm Interferometer there are three interfering waves (U0, U1 and U2). Let us assume for simplicity we will choose to make that the magnitude of the three interfering waves ('A') equal. The three interfering waves of a Single Arm Interferometer can be described in the following way:

$$U0 = A$$

$$U1 = Ae^{(-2j\beta L_1)}$$

$$U2 = Ae^{(-2j\beta L_1 - 2jkoL_2)}$$

The interference pattern produced by the interference of U0, U1 and U2 can be described as the square of the magnitude of the three interacting waves:

$$I = [U0 + U1 + U2]^2 = A^2(3 + 2\cos(2(\beta L_1 + koL_2)) + 4\cos(\beta L_1 + koL_2)\cos(\beta L_1 - koL_2))$$

This interference pattern is shown in FIG. 2(b). From this we can see that the phase of the interference pattern is related to the difference between the two paths.

$$\varphi = (\beta L_1 - koL_2)$$

Once again the phase can be used to obtain information about the test arm (described by $\beta L_1$) based on the knowledge of the reference arm (described by $koL_2$). Note that ko is the free space propagation constant (ko=$2\pi/\lambda$) where $\lambda$ is the wavelength. $L_1$ is the length of the test arm and $L_2$ is the length of the reference arm.

From the preceding discussion one can see that the interference patterns obtained by dual and single arm interferometers are equivalent since the phase of the envelope (top half of the amplitude modulation) in the case of the single arm interferometer and the phase of the actual interference pattern in the case of the dual arm interferometer is related to a difference between the two paths. FIG. 2(a) illustrates the interference patterns generated by dual arm (2 wave) interferometers and FIG. 2(b) illustrates the interference pattern generated by Single arm (3 wave) interferometers. FIG. 2 illustrates how the phase of the slowly varying 'envelope' in a Single Arm Interferometer is equivalent to the phase of the two wave interference pattern since both are a measure of the difference between two paths.

Problems with Interferometers

Interferometers require an arm with well known physical characteristics (such as free space) to act as a reference arm. Since the reference is simulated, all characteristics of the reference path are well known and any arbitrary characteristics can be chosen for the reference path. We use free space as the reference path in the examples for simplicity and by analogy to physically referenced interferometers. The use of free space in the examples is not meant to limit the generality of the virtual reference technique and the types of virtual references that can be simulated. Free space is used as it simplifies the expressions developed in later sections. The reference arm can also be used to balance the delay in the test arm (FIG. 1). The use of physical components in the reference arm, however, adds to its cost, complexity and limits its performance.

The following discussion considers the issues for an optically based reference arm in order to illustrate these issues in a tangible way. It is by no means exhaustive and serves as an example of the many issues encountered in interferometry in general. The issues can extend to an interferometer that acts on any type of wave.

The first issue in making an interferometer are that the components and labour cost of producing the reference arm are high. Since the reference path must have known spatial and material properties a free space path is often chosen as a reference. The components required to make a variable free space path (optical delay line) for the reference arm include high precision translation stages, waveguide to free space collimators and high precision adjustable mirrors/reflectors/retroreflectors. The components required can cost in the tens of thousands of dollars. The component costs, however, comprise only a fraction of the system cost. The fabrication and alignment of the free space path is extremely complex and difficult since it must achieve waveguide-to-free-space and free-space-to-waveguide coupling over the entire variable delay length. This becomes more difficult as the required variabilty increases and is especially difficult for folded free space paths that use folded optics to compress the footprint of an optical delay. Since commercial instruments would generally require a variability in the reference length of greater than 1 meter and given that optical waveguides generally have core sizes in the micron range this can mean a distance-to-target vs. target-size ratio that can be as high as a million to one, which is simply not feasible.

The next issues in creating an interferometer come from the performance limitations inherent in the free space reference arm.

The first performance issue is related to the dynamic range of the interferometer which is the variability of the reference arm. The dynamic range is limited by several factors. The first is that the translation stage itself limits the variation in the delay that can be achieved since it has a finite maximum and minimum length. The second limit on the dynamic range is that the collimation lens(es) used to couple light between fiber and free space have an optimum operating distance and the coupling loss increases as the delay is varied from this optimum. This increase in loss ultimately limits the variability of the delay depending on the amount of loss that the system can afford. The third limit on the dynamic range of the interferometer is determined by the precision with which the optics can be aligned. A longer more dynamic delay requires higher precision and tighter controls during the alignment process. Ultimately, however, a limit will be reached where higher precision is not possible and the delay cannot be made longer or more variable. The fourth limit on the dynamic range of the interferometer is determined by the how well the translation stage can maintain straight and flat axial path as it moves from one position to the next. This is important in determining whether or not the alignment can be maintained as a function of position. Ultimately, the dynamic range will be set by the combination of all four of these factors. It is no wonder why the commercially available optical delay lines do not have a very wide dynamic range.

The second performance issue is related to the step size of the translation stage, which is the smallest distance that the delay line can move. This smallest step size is a factor that determines the smallest separation between data points taken as the length of the reference arm is varied. If the system includes folded paths then the consecutive points will be separated further by twice the number of folds. As a result if the frequency of the radiation used to generate the interference is high (such as at optical frequencies) then the incremental step size must be at least sub micron so that data points taken at each position will be close enough together to produce a useful plot. This makes the requirements on the optical stage more stringent and it therefore means that a more costly stage must be used required.

The third performance limitation is due to nonidealities introduced by the reference arm. For example optics (mirrors, lenses etc) are generally introduced into the free space path and sometimes air is present in the path. What this means is that the 'free space path' is not really free space anymore because the optics and air change the reference. For example the lens introduces a small amount of dispersion in the reference path which must be known or calibrated out of the system and thus introduces error. The air flow in the free space path introduces instability related to flow and temperature fluctuations. The only way to control this issue is to use air flow and temperature stabilization techniques (i.e. placing the reference path in vacuum). This makes the system very costly.

The fourth performance issue is the time required to perform an experiment. For each data point in the experiment the system must first move the reference arm to a specified location (time) and then sample the interference pattern at that location (more time). This means that for every measurement point the system produces we must wait for it to both move and perform a scan. This severely limits the speed with which we can produce a plot with multiple data points.

The issues experienced when using a physical reference path lead to increases in the cost of interferometric systems and drastically reduce their performance. Thus, what is required is means for eliminating the physical reference path to decrease cost and increase performance.

SUMMARY OF THE INVENTION

In the first aspect of the present invention a new paradigm in interferometry is introduced in which the interferometer exists (a) partly in the physical world and (b) partly in the virtual world. The idea behind this new form of interferometry is that the parts of the interferometer that are difficult to generate or use in the physical world can be generated and used in the virtual world at (a) a lower cost and (b) higher performance.

BRIEF DESCRIPTION OF THE DRAWINGS

The invention will be better understood with reference to the drawings.

The accompanying drawings, which are incorporated in and constitute part of the specification, illustrate various example systems and methods and are not intended to limit the scope of the specification.

FIG. 8 illustrates cascaded single arm architecture for example 4 with two cascaded waveguides.

FIG. 9 illustrates an interference pattern produced by Virtual Referencing used to determine the dispersion in a test path.

FIG. 10 illustrates sample physical embodiments of an Optical Coherence Tomography system and a Radar/Lidar Range-finding system based on a Virtual Reference (Balanced) Interferometers.

DETAILED DESCRIPTION

Figure 1:
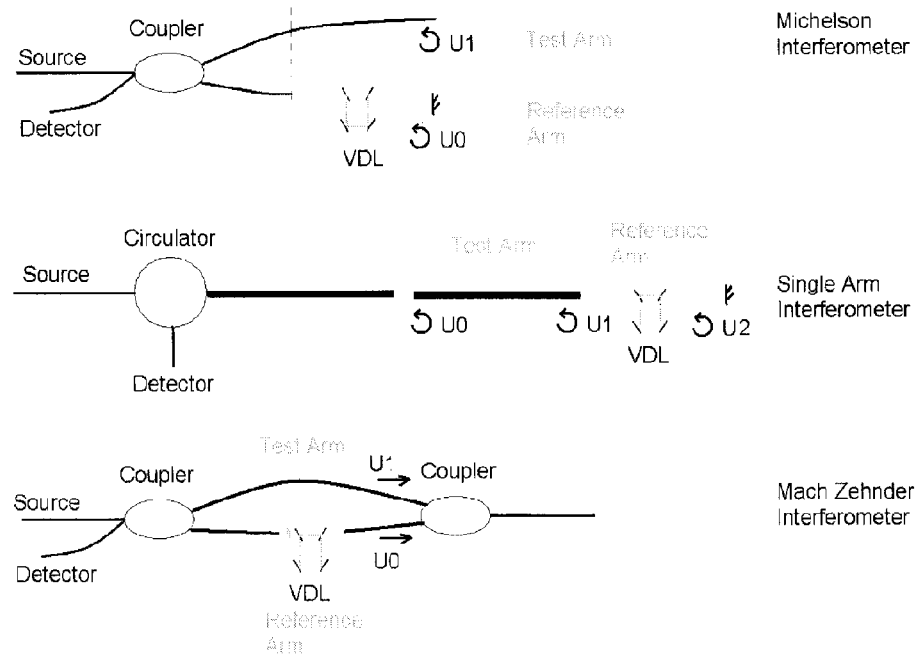
FIG. 1 illustrates examples of physically balanced/referenced interferometers in the prior art.
Figure 2A:
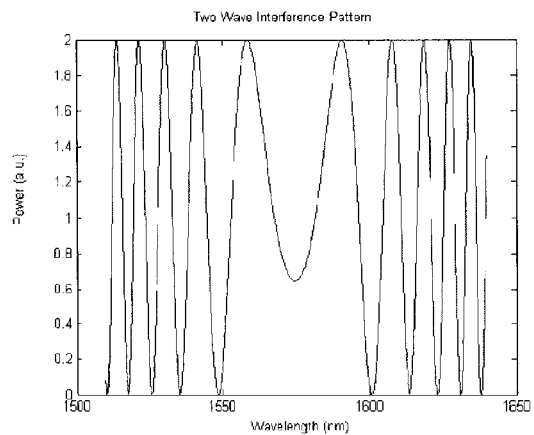
FIG. 2 illustrates an interference pattern generated in (a) a balanced Dual arm Interferometer (i.e. Michelson, Mach Zehnder etc), and (b) a balanced Single Arm Interferometer in the prior art.
Figure 2B:
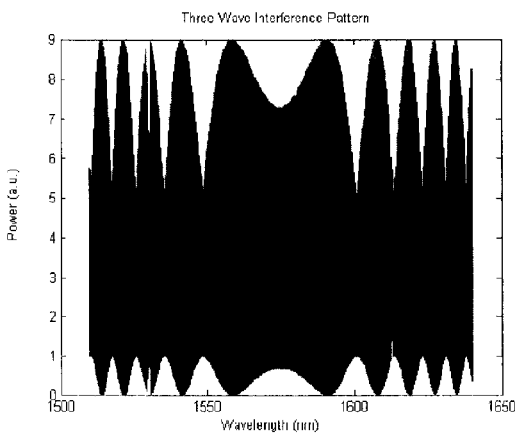

In one aspect of the present invention a new paradigm in interferometry is introduced in which the interferometer exists (a) partly in the physical world and (b) partly in the virtual world. The idea behind this new form of interferometry is that the parts of the interferometer that are difficult to generate or use in the physical world can be generated and used in the virtual world at (a) a lower cost and (b) higher performance.

In one aspect of the invention, an interferometer is provided that includes (a) physical unreferenced (unbalanced) interferometer that performs as an interferometer test arm, and (b) a means for computing a referencing sinusoid for (a), and adding frequency content to the reference sinusoid, so as to enable the generation of the interference between two or more waves.

In another aspect of the present invention a device called a Virtual Reference Interferometer (VRI) is introduced. The physical component of the interferometer of the present invention is a test arm that is provided by an unreferenced (unbalanced) interferometer that is used to generate a real (Fabry Perot) interference pattern. The "virtual" or numerically generated (simulated) component of the interferometer of the present invention is a reference arm generated by a referencing sinusoid with a frequency determined by the length of the virtual reference arm. The interferometer of the present invention is operable to calculate a virtual interference pattern based on the described physical component and the described virtual component. In other words, the Virtual Reference Interferometer of the present invention is generated by an 'operation' that relates or joins the test arm and the reference arm. This is accomplished via an operation between the physically generated interference pattern (test arm) and a virtually generated sinusoid (produced by the virtual reference arm). The length of the virtual reference arm can be varied to bring the interferometer into balance.

The virtual component may be provided by a computer linked to a computer program component. The computer program component may include computer instructions, which when made available to a computer, enable the computer to model or otherwise generate computationally the virtual component described. The computer may consist of any manner of computer device, whether a microcomputer or otherwise. The computer program component may be embedded in a computer device or appliance. It also should be understood that the computational functions described in this disclosure may be implemented to hardwire, for example, using circuit components embodying such functions.

The interferometer could be any of the many known types, including Fabry Perot, Michelson, Mach Zehnder, unreferenced single arm, or others. The interferometer of the present invention includes a wave generating source operable to emit a wave through one or more test paths and a reference path, means for generating a real interference pattern (an interferometer) from the interference caused by the propagation of the wave through the one or more test paths and reference path, and means for applying a sinusoidal operation to the real interference pattern for virtually balancing the one or more test paths and the reference path to produce a virtual interference pattern wherein the result of such operation results in a spectral interference pattern with a high frequency component and a low frequency component The low frequency component is directly proportional to the difference between the properties of the test path and the simulated 'virtual' reference path that produced the simulated reference spectral interferogram.

The method includes the steps of: (a) generating an interference pattern (via a physical interferometer component, namely an unreferenced or unbalanced interferometer); optionally this interference pattern is stored to a memory, such as a memory linked to one or more computers that are part of or linked to the system of the present invention; (b) calculating a virtual referencing sinusoid for the interference pattern of (a); (c) generating a virtual interference pattern based on (a) and (b) directly in the spectral domain with a high frequency component and low frequency component. (d) Using the low frequency component to extract the differences between the properties of the test path and the reference path.

As a further step, frequency content may be added to the interference pattern, using one or more techniques described below, so as to modulate the high frequency content to produce a low frequency component that is proportional to the differences between the physical and virtual paths. This technique, in effect, provides the reference point provided by for example free space (with its known physical path and characteristics) in a prior art interferometer.

Optionally balancing can be achieved if the frequency of the referencing sinusoid is chosen such that it creates the same balancing condition that would be created when balancing a physically balanced interferometer. This occurs when the delay experienced in the test path is the same as the delay in the reference path.

It should be noted that Virtual Referencing in accordance with the present invention is possible for any Interferometer architecture and is not limited by the type of interferometer or the type of waves being interfered. In other words it should be noted that electromagnetic or sound etc. waves may be used.

Note that the examples to follow employ the use of spectral interferometry which uses a tunable wavelength source and a detector to produce interference patterns with the wavelength as the dependent variable (can also be done spectrally using a broadband source and an optical spectrum analyzer, monochromater or tunable filter—any method that can measure optical power as a function of wavelength). This is not meant to limit the generality of this technology to spectrally acquired interference patterns. Interference patterns can also be produced by exploiting the temporal or spatial coherence of two waves. This can be done, for example, by using a broadband source, detector and a movable mirror so that the interference pattern produced is a function of the position of the movable mirror (which is located in the test path). This type of interferometry is known as temporal/spatial Interferometry. An example of this type of Interferometry is Fourier Transform Spectroscopy.

Figure 3A:
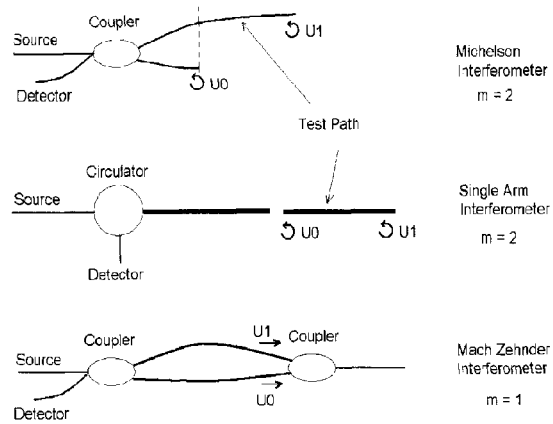
FIG. 3 illustrates (a) various unbalanced interferometer architectures and (b) interferometer architectures referenced (and/or balanced) virtually.
Figure 3B:
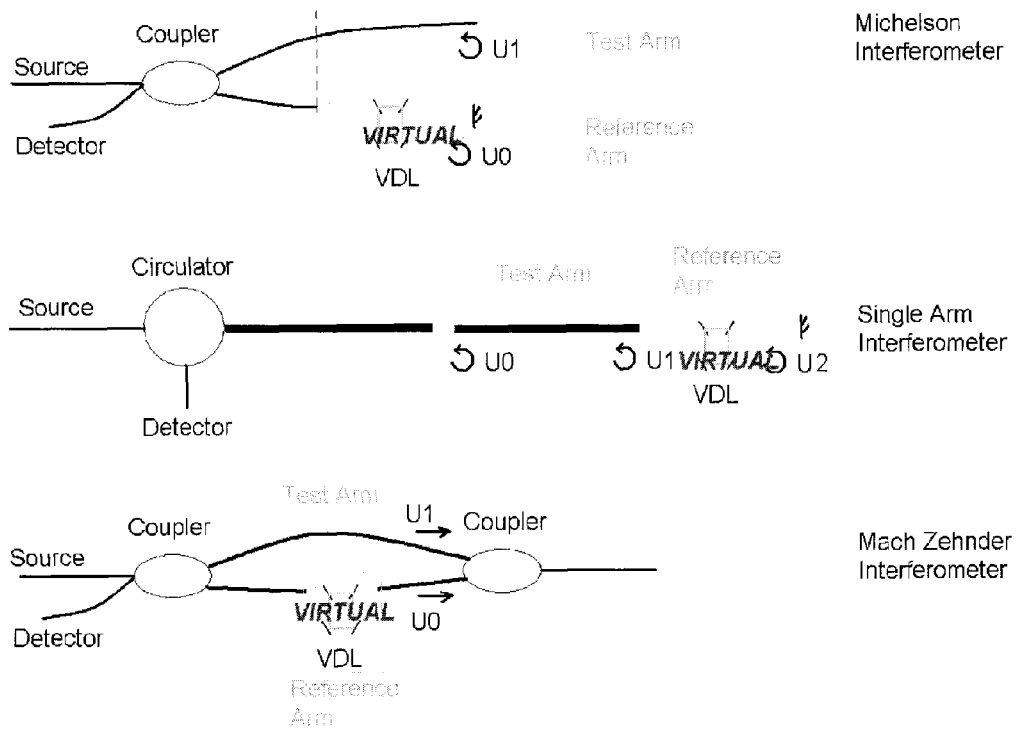

In a Virtual Reference (Balanced) Interferometer the interferometer must first be physically unbalanced. The simplest example of an unreferenced (unbalanced) interferometer is a waveguide or a cavity (seen in FIG. 3 as an unbalanced Single Arm Interferometer). The reflections from the front and back facets of the waveguide (or cavity) generate a Fabry Perot Interference Pattern which can be sampled by a detector/receiver. Note that an unbalanced interferometer produces a Fabry Perot interference pattern and therefore 'looks' the same as a waveguide or cavity to the interfering waves it generates. To illustrate this point sample architechtures of unbalanced interferometers and the interfering waves are shown in FIG. 3. Note that although the example in FIG. 3 shows a Fabry Perot Interferometer in reflection it is well known in the industry that a Fabry Perot Interferometer can be used in both reflection and transmission. We show FIG. 3 as an example and do not intend to limit the generality of the Virtual Reference Interferometer. The mathematics of the system in transmission are similar to those described below for reflection.

The real interference pattern produced by the architectures in FIG. 3 is the Fabry Perot Interference pattern described by:

$$I_{real} = [U0+U1]^2 = [U0+U0\alpha e^{(mj\beta L_{real})}]^2$$

$$I = U0^2(1+\alpha^2-2\alpha \cos(mL_{real})) = I_0 + I_1 \cos(m\beta L_{real}) \qquad \text{Eq. 1}$$

Where U0 represents the wave in the first path, U1 represents the wave in the second path, $\alpha$ is the loss factor between U0 and U1 and m is the number of passes the wave (light) makes along the two paths (i.e. If light makes a single pass before interfering (as in the Mach Zehnder) then m=1, if light is reflected back and makes two passes along a path before interfering (Michelson or Single Arm) then m=2). $L_{real}$ is the physical length difference between the two paths. Note that for simplicity we have only considered the first order reflections from the facets of the interferometer. The higher order reflections will add frequency content which will be a multiple of the first order frequency but have no effect on the end result. We can perform the virtual balancing with any of these frequencies as well but we will take for simplicity the first order in this description. Note, however, we do not intend to limit the generality of our description.

Figure 4:
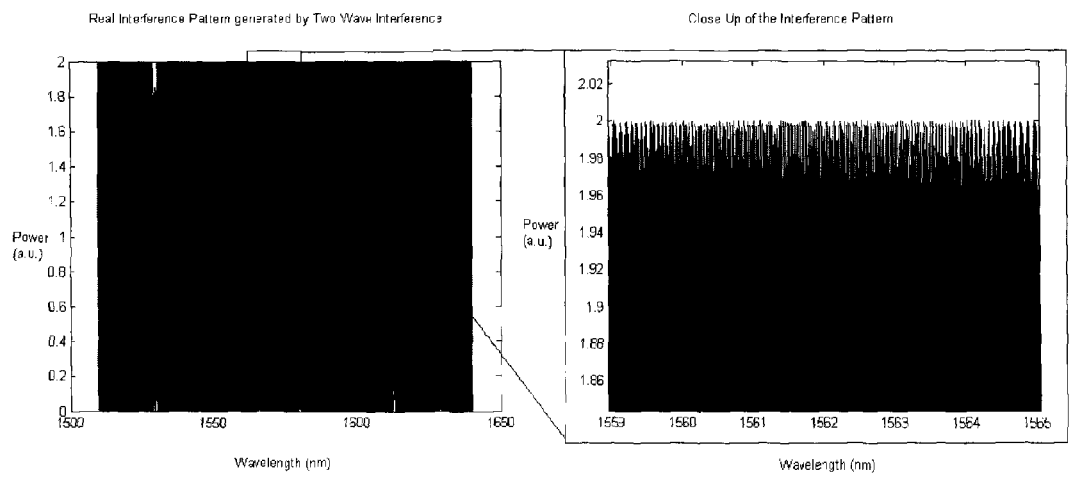
FIG. 4 illustrates a Fabry Perot interference Pattern generated by an unbalanced interferometer.

Note that Eq. 1 is a general expression for the interference pattern produced by these two reflections. Also if the medium between U0 and U1 is vacuum then p reduces to ko, the propagation constant of free space (ko=$2\pi/\lambda$) and $\alpha$=1 (no loss). A sample interference pattern for the architectures shown in FIG. 3 is illustrated in FIG. 4. The frequency of the interference fringes depends on the length of the test arm and the propagation constant (defined later as (3) in the test arm.

Note that FIG. 3 shows fiber based architectures but the results hold true regardless of architecture (free space or fiber based interferometer) or type of wave interfered (i.e. Holds true for sound and other waves). FIG. 3 is not meant to limit the generality of Virtual Reference Interferometry only to show a single tangible case. Also the source and receiver can be any wave generating source such as, for example an RF source, microwave source, laser source, broadband source, X-ray source, sound wave generator etc. The detector/receiver can be any wave receiver such as for example an RF receiver, microwave receiver, laser detector, broadband receiver (optical spectrum analyser), X-ray detector, sound wave receiver. The discussion that follows assumes the use of a tunable laser as the source and a laser detector as the receiver. The interference pattern produced by this pair is a spectral interference pattern in which the amplitude is plotted as a function of wavelength. The choice of this pair for the source and detector is only to simplify the discussion and illustrate tangibly the issues related to using a physical reference and are not meant to limit the generality of the discussion.

Note that the following discussions involve the use of spectral interferometry which uses a tunable wavelength source and a detector to produce interference patterns with the wavelength as the dependent variable (can also be done spectrally using a broadband source and an optical spectrum analyzer, monochromater or tunable filter). This is not meant to limit the generality of this technology to spectrally acquired interference patterns. Interference patterns can also be produced by exploiting the temporal or spatial coherence of two waves. This can be done, for example, by using a broadband source, detector and a movable mirror so that the interference pattern produced is a function of the position of the movable mirror (which is located in the test path) This type of Interferometry is temporal/spatial in nature. An example of this type if Interferometry is Fourier Transform Spectroscopy.

Loss Factor

From this interference pattern the loss (or gain) experienced between U0 and U1 can be determined. This loss is represented by the loss (or gain) factor, a, which can be determined by examining the ratio between the amplitude of the interference sinusoid and its (DC) offset.

$$C = \frac{I_1}{I_0} = \frac{(2\alpha)}{(1+\alpha^2)} \qquad \text{Eq. 2}$$

Where C is the ratio between the amplitude of the sinusoid to its offset. Given C the loss (or gain) factor can be determined as:

$$\alpha = \left(\frac{1}{C}\right) \mp \left(\left(\frac{1}{C^2}\right) - 1\right)^{0.5} \text{ where } I_1 = 2\alpha \qquad \text{Eq. 3}$$

For the measurement of loss the '−' solution is taken and for the measurement of gain the '+' solution is taken.

Virtual Referencing

A Virtual Reference (and balanced) Interferometer is generated by an 'operation' between a real interference pattern and a virtually generated sinusoid (or set of sinusoids). This operation, therefore, transforms a real (Fabry Perot) interference pattern (given by Eq. 1) into a virtual interference pattern. Note that we can also virtually balance the interferometer by appropriate selection of the virtual length represented by the virtual referencing sinusoid.

Since the propagation constant of free space is known exactly (i.e. $k_0=2\pi/\lambda$), it can be easily represented virtually (simulated). A more general reference path may also be simulated virtually by replacing $k_0$, with the more general propagation constant $\beta$ in the equations, however, for our examples the use of free space ($k_0$), is preferred as it will help to simplify the mathematical derivations used to illustrate the extraction of group delay and second order dispersion in the later analysis.

Examples of some possible 'operations' between the physical and virtual components are given in the following section. These examples are not meant to be exhaustive but only to illustrate how Virtual Referencing (and/or Balancing) is achieved. It should be understood that the operation selected will depend on the matter being analyzed using the interferometer. It should be understood that the computer program component of the present invention can provide means for suggesting, based on user input, application of one or more possible operations. It should be understood that for many applications the multiplication of a virtual sinusoid operation will be used.

EX. 1

Addition of a Virtual Sinusoid

We can add a sinusoid to the real interference pattern $I_{real}$ in order to virtually reference it. Let us choose a virtual referencing sinusoid to be $$I_0 \cos(mkoL_{virtual}) \text{ and set } m=2$$

Where $I_0$ is a factor that makes the amplitude of the sinusoid the same as the amplitude of the sinusoid in $I_{real}$. Therefore when the virtually generated sinusoid is added to the real interference pattern the result is a virtual interference pattern that can be described as $$I_{virtual}=I_{real}+I_0 \cos(2koL_{virtual})$$

Where $ko=2\pi/\lambda$, is the propagation constant of free space and $L_{virtual}$ is chosen to be the length of a physical free space path that would be required to balance the real path (in a physically referenced interferometer).

Let us examine the effect of this sinusoidal addition on the interference pattern.

$$I_{virtual}=I_0+I_1 \cos(2\beta L_{real})+I_1 \cos(2kOL_{virtual})$$

$$I_{virtual}=I_0+2I_1(\cos(\beta L_{real}+koL_{virtual})\cos(\beta L_{real}-koL_{virtual}))$$

Figure 5:
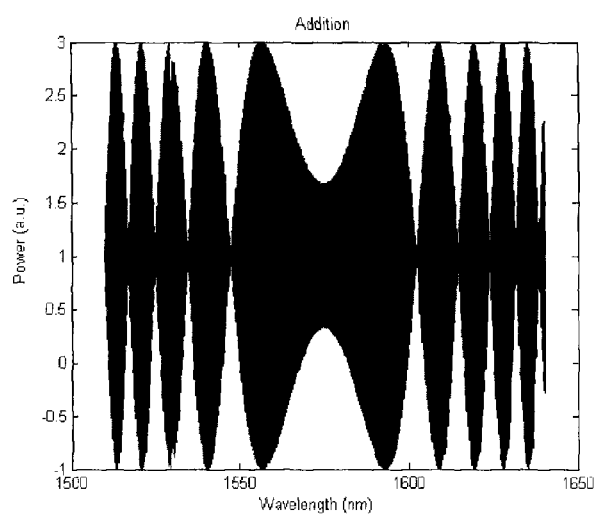
FIG. 5 illustrates Virtual Referencing with addition.

The result is an interference pattern with a high frequency component ($\beta L_{real}+kOL_{virtual}$) and a low frequency component ($\beta L_{real}-kOL_{virtual}$) which amplitude modulates the high frequency component creating an 'envelope' in the interference pattern. We can easily see that this low frequency component provides us with a difference between two alternate paths (a real one and a virtual one that represents free space). This is therefore by definition an interferometer. The interference pattern generated by virtual referencing with addition is shown in FIG. 5 where the frequency of the referencing sinusoid has been chosen to balance the interferometer (at a given wavelength). Note that the DC component and the high frequency carrier may be filtered out leaving us with:

$$I_{virtual}=\cos(\beta L_{real}-koL_{virtual})$$

EX. 2

Subtraction of a Virtual Sinusoid

If subtraction is chosen as the 'operation' between the real and virtual parts of the interferometer a similar result is obtained. For this example let us choose cos( ) and m=2 again.

$$I_{virtual}=I_{real}-I_0 \cos(2koL_{virtual})$$

Examining the effect of the subtraction on the interference pattern.

$$I_{virtual}=I_0+I_1 \cos(2\beta L_{real})-I_1 \cos(2koL_{virtual})$$

$$I_{virtual}=I_0-2I_1(\sin(\beta L_{real}+koL_{virtual})\sin(\beta L_{real}-kOL_{virtual}))$$

Figure 6:
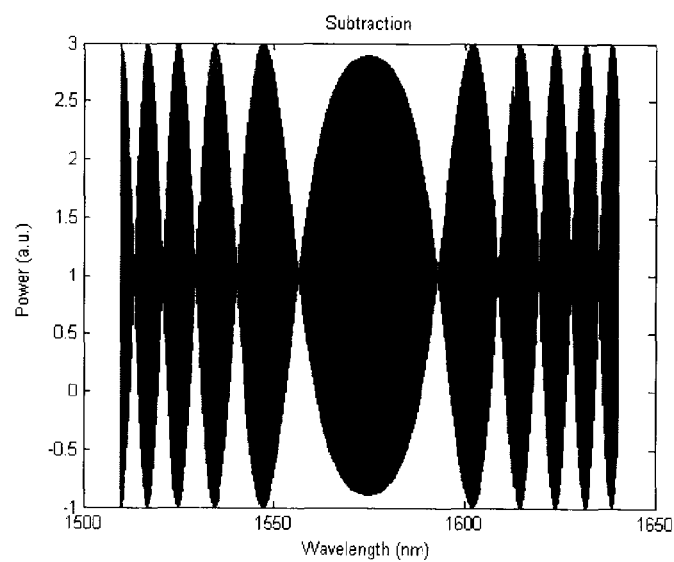
FIG. 6 illustrates Virtual Referencing with subtraction.

As before this generates an interference pattern with a high frequency component ($\beta L_{real}+koL_{virtual}$) and a low frequency component ($\beta L_{real}-koL_{virtual}$). The low frequency component amplitude modulates the high frequency component creating the 'envelope' of the interference pattern. We can easily see that this low frequency component provides us with a difference between two alternate paths (a real one and a virtual one that represents free space). This is therefore by definition an interferometer. The interference pattern generated by virtual referencing with subtraction is shown in FIG. 6 where the frequency of the referencing sinusoid (determined by $L_{virtual}$) has been chosen to balance the interferometer (at a given wavelength). Note that the DC component and the high frequency carrier may be filtered out leaving us with:

$$I_{virtual}=\sin(\beta L_{real}-koL_{virtual})$$

EX. 3

Multiplication of a Virtual Sinusoid

If multiplication of a sinusoid was chosen as the 'operation', a similar result is obtained. Let us choose cos( ) and m=2 again in this example.

$$I_{virtual} = I_{real} \cos(2koL_{virtual})$$

Examining the effect of multiplication on the interference pattern.

$$I_{virtual} = (I_0 + I_1 \cos(2\beta L_{real}))\cos(2koL_{virtual})$$

$$I_{virtual} = (I_0 \cos(2koL_{virtual}) + I_1 \cos(2\beta L_{real})\cos(2koL_{virtual}))$$

$$I_{virtual} = I_0 \cos(2koL_{virtual}) + \frac{I_1}{2}(\cos(2\beta L_{real} + 2koL_{virtual}) + \cos(2\beta L_{real} - 2koL_{virtual}))$$

Figure 7:
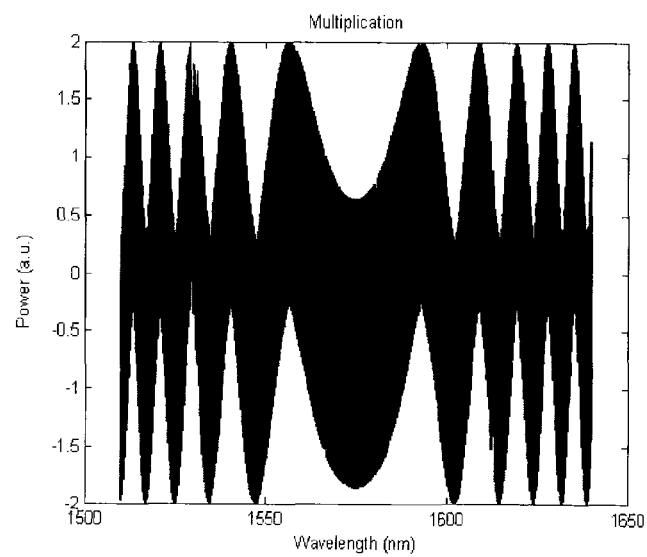
FIG. 7 illustrates Virtual Referencing with multiplication.
Figure 7B:
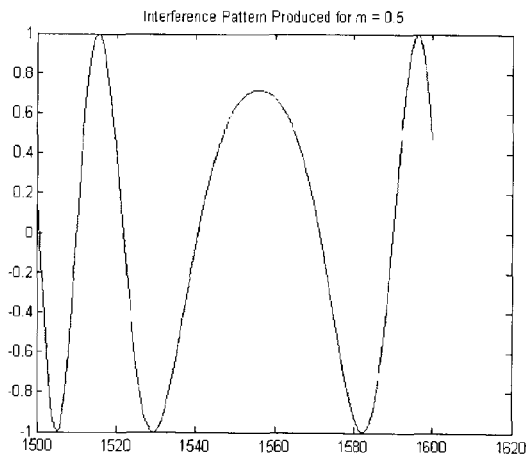
Figure 7C:
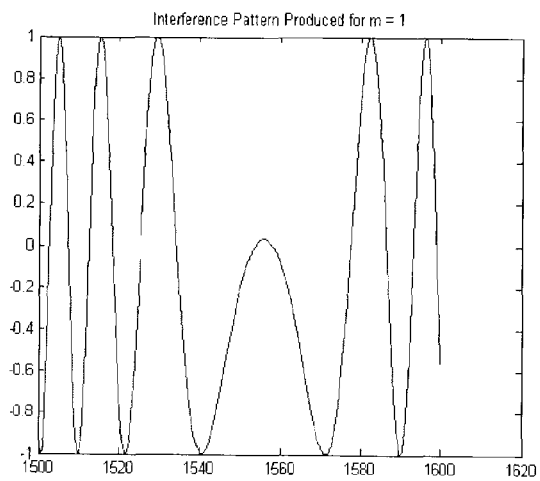
Figure 7D:
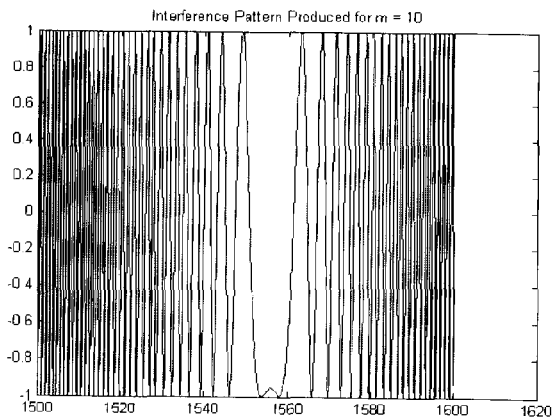
Figure 7E:
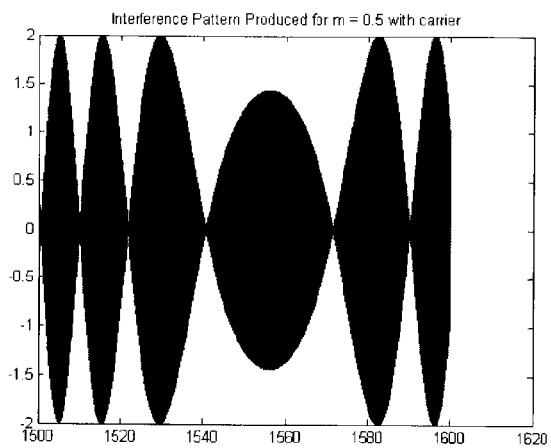
Figure 7F:
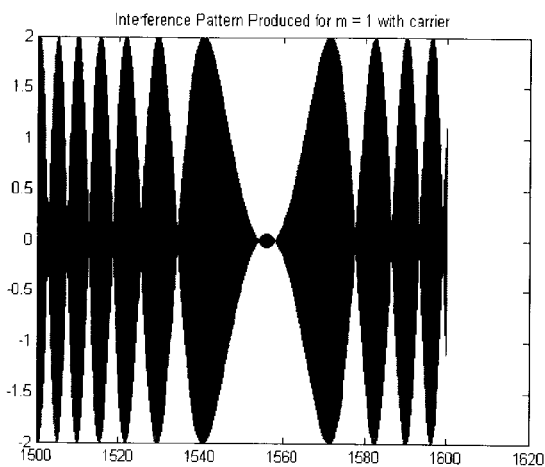
Figure 7G:
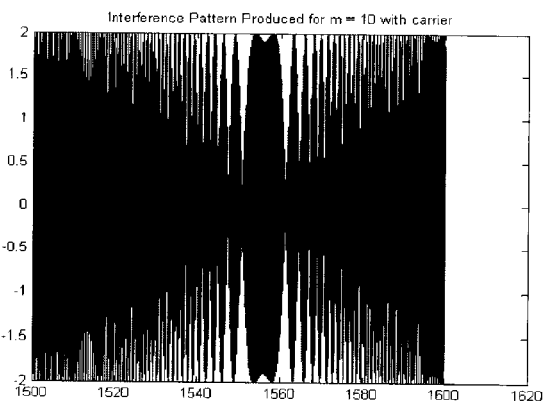

The result is an interference pattern with a high frequency components ($2koL_{virtual}$) and ($2\beta L_{real} + 2koL_{virtual}$) and a low frequency component ($2(\beta L_{real} - koL_{virtual})$) which amplitude modulates the high frequency component creating the 'envelope' of the interference pattern. We can easily see that this low frequency component provides us with a difference between two alternate paths (a real one and a virtual one that represents free space). This is therefore by definition an interferometer. The interference pattern generated by virtual referencing with multiplication is shown in FIG. 7 where the frequency of the referencing sinusoid has been chosen to balance the interferometer (at a given wavelength). For example, in FIGS. 7b-7g, it can be seen that when m is fractional (as in FIG. 7b), the bandwidth required is increased, while when m is greater than 1 the bandwidth required is reduced as the interference pattern is compressed. FIGS. 7b-7d illustrate Virtual Referencing with dynamic bandwidth capability for various values of m, while FIGS. 7e-7g illustrate Virtual Referencing with dynamic bandwidth capability for various values of m after multiplication by a high frequency carrier.

Note that the high frequency components may be filtered out leaving us with:

$$I_{virtual} = \cos(\beta L_{real} - koL_{virtual})$$

If instead of multiplying by cos( ) we had chosen to multiply by sin( ) the result would be:

$$I_{virtual} = I_0 \sin(2koL_{virtual}) + \frac{I_1}{2}(\sin(2\beta L_{real} + 2koL_{virtual}) - \sin(2\beta L_{real} - 2koL_{virtual}))$$

Again similar to the result with cos( ) Where the high frequency carriers may be filtered out leaving us with:

$$I_{virtual} = \sin(\beta L_{real} - koL_{virtual})$$

EX. 4

Cascaded System

The present invention also provides means for virtual referencing on a cascaded system of a plurality of waveguides. If we take for example a Single Arm Interferometer architecture with 2 cascaded waveguides with different length and different propagation constants. For simplicity we will also assume that there is no loss. The cascaded Single Arm Interferometer architecture for this example is given in FIG. 8.

Given $L_{real1}$ as the length of the first waveguide and $L_{real2}$ as the length of the second waveguide and $\beta_1$ and $\beta_2$ as the propagation constants of each waveguide respectively then the real interference pattern for this configuration is given by:

$$I_{real} = U0^2 (3 + 2 \cos(2\beta_1 L_{real1}) + 2 \cos(2\beta_2 L_{real2}) + 2 \cos(2\beta_1 L_{real1} + 2\beta_2 L_{real2}))$$

$$I_{real} = I_0 + I_1 \cos(2\beta_1 L_{real1}) + I_1 \cos(2\beta_2 L_{real2}) + I_1 \cos(2\beta_1 L_{real1} + 2\beta_2 L_{real2})$$

If for example we choose addition as the operation linking the real and the virtual parts of the Virtual Reference Interferometer then the virtual interference pattern produced is given by:

$$I_{virtual} = (I_0 + I_1 \cos(2\beta_1 L_{real1}) + I_1 \cos(2\beta_2 L_{real2}) + I_1 \cos(2\beta_1 L_{real1} + 2\beta_2 L_{real2})) + I_1 \cos(2koL_{virtual})$$

Where the referencing sinusoid can be chosen to balance the second, third or fourth term depending on the length chosen for $L_{virtual}$. Balancing the second term is equivalent to only balancing the first waveguide. Balancing the third term is equivalent to balancing only the second waveguide. Balancing the last term is equivalent to balancing both waveguides. Note that similar results would be obtained if an alternative operation such as for example multiplication was chosen or if the cascaded system included more elements.

General Form

Virtual Balancing in general can be achieved by operating on the real interference pattern with a set of sinusoids:

$$\Sigma(n(\cos(mkoL_{virtual1} + \phi_{virtual1}))^k + p(\sin(mkoL_{virtual2} + \phi_{virtual2}))^l) \qquad \text{Eq. 4}$$

Note: The phase offset $\phi_{virtual1}$ and $\phi_{virtual2}$ only changes the phase of the central peak in the interference pattern.

The above examples show how spectral content can be added virtually to a physically generated interference pattern via addition, subtraction and multiplication with a virtually generated sinusoid. What is important is that spectral content is added to the physically generated interference pattern. As a result if we were to take the Fourier Transform of the physically generated interference pattern, add the spectral content directly in the Fourier domain (no sinusoid necessary) and then take the inverse Fourier Transform we would observe the same results as above. We have illustrated the examples in the way shown above to provide a better understanding of Virtual Referencing.

Balancing a Virtual Reference Interferometer: Determining $L_{virtual}$ and $N_G$ An interferometer is balanced when the delay of a light beam (or wave in general) in the reference arm is the same as the delay in the test arm (i.e. the delay length in both arms is the same). If we take the case of a reference arm with a free space optical delay then this occurs when:

$$L_{reference} = N_{Gtest} L_{test}$$

In a Virtual Reference Interferometer the reference length is virtual (represented by a sinusoid). There are several ways to determine the virtual length required to balance the interferometer. The first is to know the group index, $N_G$, of the material in the test arm. If the test arm is free space then this index is simply 1. The virtual length can then be calculated as:

$$L_{virtual} = N_G L_{real} \qquad \text{Eq. 5}$$

If, however the group index is not known then $N_G$ and therefore $L_{virtual}$ can be determined in one of the following ways depending on the operation used. Note, however, that there are multiple methods for achieving this balancing and the following methods are only examples.

Method 1: If Addition or Subtraction is Used

When addition or subtraction of a virtual referencing sinusoid is used as the operation to balance the interferometer there are two frequencies present in the virtual interference pattern (excluding DC). The two frequencies are ($2\beta L_{real}$) generated by the real part of the interferometer and ($koL_{virtual}$) generated by the virtual part of the interferometer. The interference pattern generated will be the result of the mixing of these two frequencies to give a high frequency component ($\beta L_{real}+koL_{virtual}$) and a low frequency component ($\beta L_{real}-koL_{virtual}$) which will produce the 'envelope'. The goal, therefore, is to make the 'envelope' (low frequency component) as small as possible. To do this the virtually generated frequency of ($koL_{virtual}$) must be made equal to ($2\beta L_{real}$). This can be done in the following way.

1. Perform a frequency domain analysis on $I_{real}$ i.e. Perform an FFT on $I_{real}$ with a given sampling frequency, $f_s$ and a given number of sampling points M.
2. The FFT of $I_{real}$ will give a peak at DC (0) and a series of closely spaced peaks which correspond to the $2\beta(\lambda)L_f$ frequency components in $I_{real}$. Choose one of these peaks say the centre one at p. This corresponds to the frequency component $$2\pi \frac{f_s}{M} p$$

or the wavelength $$\lambda_p = \frac{M}{(2\pi f s p)}$$

Note: We can choose a small section of $I_{real}$ centred at $\lambda_p$ and take the FFT of this small section if we only want this peak.

3. Generate a virtual balancing sinusoid using an arbitrary value of $L_{virtual\ 2}$ and perform an FFT with the same parameters $f_s$ and M as in step 1. The peak will be located at a point k. This corresponds to the frequency component $$2\pi \frac{f_s}{M} k$$

or the wavelength $$\lambda_p = \frac{M}{(2\pi f s k)}$$

4. Generate a second virtual balancing sinusoid using value of $L_{virtual\ 2}$ that is different from the first and perform an FFT using the same parameters $f_s$ and M as in step 1. The peak will be located at r. This corresponds to the frequency component $$2\pi \frac{f_s}{M} r$$

or the wavelength $$\lambda_p = \frac{M}{(2\pi f s r)}$$

Note: r can be 0 in which case this step can be ignored

5. Steps 3 and 4 are used to generate the relationship between a spatial separation and the corresponding spectral separation for the given parameters of the FFT. This relationship is used to determine $L_{virtual}$.

$$\frac{(spatialsep_1)}{(spectralsep_1)} = \frac{(spatialsep_2)}{(spectralsep_2)} \qquad \text{Eq. 6}$$

$$(spatialsep_2) = (spectralsep_2)\frac{(spatialsep_1)}{(spectralsep_1)}$$

$$(L_{virtual} - 0) = \left(2\pi \frac{f_s}{M}\right)(p-0)\frac{((L_{virtual2} - L_{virtual1}))}{\left(\left(2\pi \frac{f_s}{M}\right)((r-k))\right)}$$

$$L_{virtual} = \frac{p}{((r-k))}((L_{virtual2} - L_{virtual1}))$$

6. Therefore a sinusoid with the frequency ($2koL_{virtual}$) will produce a peak that overlaps with the one at p in $I_{real}$ and virtually balance the interferometer to generate $I_{virtual}$ Method 2: If Multiplication is Used When multiplication of a virtual referencing sinusoid is used as the operation to balance the interferometer there are tree frequencies present in the virtual interference pattern (excluding DC). These three frequencies are ($2kOL_{virtual}$), ($2\beta L_{real}+2koL_{virtual}$) and ($2\beta L_{real}-koL_{virtual}$)). The frequency component will be used to produce the 'envelope'. The goal, therefore, is to make the 'envelope' (low frequency component) as small as possible. To do this we must bring this component as close as possible to zero. This can be done in the following way.

1. Perform a frequency domain analysis on a small wavelength section of $I_{virtual}$ using a small value for virtual reference path length, $L_{virtual\ 1}$. There will be three peaks: the first peak will correspond to the frequency component ($2koL_{virtual}$) if $L_{virtual\ 1}$ is chosen small enough, the second peak should then correspond to ($2\beta L_{real}-koL_{virtual\ 1}$)) and the third to ($2\beta L_{real}+2koL_{virtual\ 1}$). We are interested in the second peak since it will generate the 'envelope'. This second peak will be located at point k.
2. Generate a second virtual balancing sinusoid using a value of $L_{virtual\ 2}$ that is different from the first and perform a frequency domain analysis on the same small wavelength section as in step 1. Use the same parameters $f_s$ and M as in step 1. The peak will be located at r.
3. Steps 3 and 4 are used to generate the relationship between a spatial displacement and a spectral displacement for the given parameters of the FFT $f_s$ and M. This relationship is used to determine the amount to increase $L_{virtual}$.

$$\frac{(spatialdisp_1)}{(spectraldisp_1)} = \frac{(spatialdisp_2)}{(spectraldisp_2)}$$

$$(spatialdisp_2) = (spectraldisp_2)\frac{(spatialdisp_1)}{(spectraldisp_1)}$$

4. There are two possibilities for a reference point. We can either choose $L_{virtual\ 1}$ or $L_{virtual\ 2}$. If we were to choose $L_{virtual\ 1}$ as the reference point then the spatial displacement required would be.

$$(\Delta L_{virtual1}) = (k)\frac{((L_{virtual2} - L_{virtual1}))}{(((r-k)))}$$

and the value of $L_{virtual}$ would be calculated as:

$$L_{virtual} = L_{virtual1} + \Delta L_{virtual1}$$

5. There are two possibilities for a reference point. We can either choose $L_{virtual\ 1}$ or $L_{virtual\ 2}$. If we were to choose $L_{virtual\ 1}$ as the reference point then the spatial displacement required would be.

$$(\Delta L_{virtual2}) = (r)\frac{((L_{virtual2} - L_{virtual1}))}{(((r-k)))}$$

and the value of $L_{virtual}$ would be calculated as:

$$L_{virtual} = L_{virtual2} + \Delta L_{virtual2}$$

Therefore a sinusoid with the frequency ($2koL_{virtual}$) will minimize ($2\beta L_{real} - koL_{virtual\ 1}$)) virtually balance the interferometer.

We can therefore calculate $L_{virtual}$ and $N_G(\lambda)$ (via Eq. 5) for whatever wavelength we choose.

Dynamic Balancing Capability & the Dynamic Bandwidth Advantage

One of the most important benefits of using Virtual Reference Interferometers is their capability to dynamically change the amount of bandwidth they require to produce an interference pattern. In a physically referenced interferometer the reference arm can balance the interferometer at only one length. In a Virtual Reference Interferometer the reference arm can balance the interferometer at multiples of the balanced length and this will cause the interference pattern to become 'compressed' by the same factor so that it can fit in a smaller bandwidth range. If the interference pattern is 'compressed' this can permit the use of lower cost lasers for example.

To illustrate this point we will consider a Virtual Reference Interferometer that uses multiplication as the referencing operation and balance it according to method #2 to find the first order virtual balance length, $L_{virtual}$.

If instead we are to use the virtual balancing length $2L_{virtual}$ then we would still find that the interference pattern is balanced, however, it will be compressed by approximately a factor of two. Thus we would only require half the bandwidth as in the first order case. The bandwidth compression works best for multiples of $L_{virtual}$ (i.e. $2L_{virtual}$, $3L_{virtual}$, $4L_{virtual}$, $5L_{virtual}$ ...) but also works for multiples with an additional factor of two (i.e. $1.125L_{virtual}$, $1.25L_{virtual}$, $1.5L_{virtual}$) $1.75L_{virtual}$, $2.25L_{virtual}$ ...)

A limit, however, exists on the maximum amount of compression possible. The limit is determined by the fact that the contrast ratio of the envelope is reduced along with the bandwidth. Therefore the minimum requirement in the contrast of the envelope will determine the maximum amount the bandwidth can be compressed. There is a method for increasing the envelope contrast ratio by taking the individual points in the interference pattern to a higher power. We will discuss this in the next section.

Compensating for Contrast Ratio Reductions

The effect of bandwidth compression is that the contrast ratio of the fringes is reduced. This effect can be compensated for by taking the individual points in the interference pattern and exaggerating their relative positions by taking their magnitudes to a power.

$$I_{Virtual} = I_{Virtual}^n$$

Optimum Compensation Scheme

In order to achieve the optimum compensation the following procedure is introduced.

1. The real interference pattern must have the DC component filtered out and its magnitude normalized.

$$I_{real} = U0^2(1+\alpha^2 + 2\alpha \cos(mL_{real})) = I_0 + I_1 \cos(m\beta L_{real}) = \cos(m\beta L_{real})$$

2. The virtual referencing sinusoid must be chosen such that the referencing length is a multiple of the virtual reference length so that the interference pattern is symmetric across the horizontal axis. Since we have filtered out and normalized the real interference pattern the virtual reference sinusoid is given for example as:

$$I_{virtual} = (\cos(2\beta L_{real} + 2CkoL_{virtual}) + \cos(2\beta L_{real} - 2CkoL_{virtual}))$$

Where C is the compression factor.

3. Since the interference pattern is now symmetric if we take the individual points in it to a power of n, where n is a positive integer, then all points will be positive. This effectively increases the number of points in the carrier and better defines the envelope.

Another method that is immune to envelope contrast ratio reductions is introduced in the next section.

Dynamic Bandwidth Methods Immune to Envelope Contrast Ratio Reduction

This section introduces methods for dynamically changing the bandwidths without reducing the contrast ratio of the envelope. There are several methods of reaching the final equation but the resulting equation is generally the same.

If we let $\beta$ represent the propagation constant of the wave (i.e. light) whether it is in free space or in a material then our equations will be in general form. The following are two examples of how the required bandwidth can be increased or decreased with Virtual Reference Interferometry. We will show how this can be achieved for the case of Virtual Referencing by multiplication as an example. Similar results can be attained using Virtual Referencing by other operations (i.e. addition, subtraction etc.)

From Eq. 1 we have:

$$I_{real} = [U0 + U1]^2 = [U0 + U0\alpha 0^{(mj\beta L_{real})}]^2$$

$$I = U0^2(1 + \alpha^2 + 2\alpha \cos(m\beta L_{real})) = I_0 + I_1 \cos(m\beta L_{real})$$

If we filter out the DC term, $I_0$, and divide by the amplitude, $I_1$, we get:

$$I_{ini} = \cos(m\beta L_{real})$$

If we let:

$$u = m\beta L_{real}$$

and $$v = mkoL_{virtual}$$

Where u is the phase term of the real sinusoid generated by the fabry perot fringes and v is the phase term for the virtual reference sinusoid that balances u.

Method #1

If we filter out the DC term, $I_0$, and divide by the amplitude, $I_1$, we get:

$$I=\cos(m\beta L_{real})$$

Now we can apply Virtual Referencing to get:

$$I_{v0}=\cos(m\beta L_{real}) \times 2\cos(mk o L_{virtual})$$

$$I_{v0}=\cos(m(u+v))+\cos(m(u-v))$$

Filtering out the high frequency term gives:

$$I_{Vm0}=\cos(m(u-v))$$

This term can now be squared and filtered to achieve compression.

Method #2

Taking the $\cos^{-1}(I_{init})$ gives us u:

Since we already have v we can simply substitute into the expression derived in Method #1.

$$I_{Vm}=\cos(m(u-v))$$

Where m is the bandwidth compression or expansion factor. If m is fractional then it will cause the fringes to expand and require more bandwidth. If m is a number greater than 1 then it will cause the fringes to compress and therefore use less bandwidth.

Examples of the interference patterns generated for different values of m (the compression or expansion factor are given in FIGS. 7b-d.

Note that we can choose to operate (i.e. multiply, add, subtract) on $I_{vn}$, using a high frequency cosine if we wish to obtain an inteference pattern with an envelope on a high frequency carrier.

$$I_{VmS}=\cos(m(u-v))\cos(s)$$

Examples of the interference patterns generated for different values of m (the compression or expansion factor) are shown in FIG. 7e-g. In these examples s was chosen to be equal to v. In general if s has a low frquency close to zero then the equation reduces to:

$$I_{Vm}=\cos(m(u-v))$$

Note that the Dynamic bandwidth capability is very useful for shrinking the required bandwidth to sub nanometer levels. This is very useful in low bandwidth intensive applications such as Dense Wave Division Multiplexing test and measurement.

The Phase of a Compressed Interference Pattern

The phase of a virtually referenced interference pattern contains a sinusoid with frequency $$\phi_{envelope}=mC(\beta L_{real}-koL_{virtual})=mC(n_{eff}koL_{real}-koL_{virtual})$$

Where m depends on the type of interferometer used and C is the compression factor.

Method #3

One may also produce a compressed (or expanded) envelope by simulating a virtual reference which contains dispersion. In this case $\beta_{virtual}$ replaces $k_0$ in the above expressions and the second (and higher) order dispersion components of the virtual reference arm are combined with those in the physical test path. When the difference between the higher order components (i.e. second order dispersion) of the physical (test) and virtual (reference) paths is large this results in compression. When the difference between these components is small the result is expansion of the required bandwidth. When the simulated virtual reference contains dispersion, the phase of the virtually referenced interference pattern is given by:

$$\phi_{envelope}=m(\beta L_{real}-\beta_{virtual}L_{virtual})$$

Where both $\beta$ and $\beta_{virtual}$ may be Taylor expanded to describe the differences between the higher order terms. Since $n_{eff}(\lambda)$ is a general function of wavelength ($\lambda$), it may be described by a simulated polynomial and the higher order dispersion terms can therefore be differentiated and calculated. The exact expressions depend on the polynomial used. The mathematical description for the simplest case where $\beta_{virtual}=k_0$ (i.e. $n_{eff}(\lambda)=1$ and higher order terms =0) is shown in detail in Eq. 7 of the next section.

The Innovation

The novelty of the innovation is that the interferometer is part real and part virtual. The virtual part is the part that is most difficult to generate physically, the reference arm. By generating the reference arm virtually the reference functions well relative to the need since free space is simulated and the instabilities and nonidealities of a real reference are eliminated. The use of the virtual reference also allows for increased performance and reduced bandwidth requirements for the interferometer.

The value of the innovation is that a virtually balanced (Referenced) interferometer can produce measurements with the same (or better) precision and accuracy as a physically referenced (balanced) interferometer without the high costs and performance issues associated with creating a physical delay. The proof that the performance is the same or better with a Virtual Reference (balanced) Interferometer is that the phase of the 'envelope' of the virtual interference pattern is equal to the phase generated in a physically referenced (balanced) interferometer with a real interference pattern created using a real test path and reference path.

A comparison between Physically Balanced (Referenced) and Virtual Reference (balanced) Interferometers is shown in the table below.

| Physically Referenced & Balanced Interferometer | Virtual Reference & Balanced Interferometer |
| --- | --- |
| Hardware Implementation | Software Implementation |
| Expensive real components | Free virtual components |
| Limited dynamic range | Large dynamic range |
| Translation stage limit | |
| Alignment issues | |
| Optics issues (collimation & loss) | |
| Requires costly alignment | Alignment free |
| Reference length calibration error due to presense of collimating lens | Error free |
| Reference length calibration error due to dispersion of collimating lens | Dispersion free |
| Stability issues related to temperature and air flow fluctuations in the free space path | Stable |
| Smallest step size in micron range-widely spaced data points | Infinitesimal step size (smallest number computer can produce)-closely spaced data points |
| Slow-the source (laser/OSA) must scan for each data point | Fast-multiple data points from a single scan. |
| Static Bandwidth | Dynamic Bandwidth |
| Large bandwidth required cannot be reduced | capability for reduction (or increase) in bandwidth requirements |

Sample of the Potential Applications of this Technology

1. Waveguide/Fiber or Cavity Testing—Loss, Dispersion, Spectroscopy & Chemical Analysis, Electrical/Electronics Testing 2. Tomography and Profilometry Applications (i.e. Optical Coherence Tomography, Surface profiling & Imaging)
3. Lidar and Radar and Rangefinding—Distance metrology in general
4. Thermal Sensing
5. Tension & Stress Sensing
6. Ultrasound & Sonography
7. Sonar
8. Anywhere there is interference 1. Waveguide/Fiber or Cavity Testing & Spectroscopy The measurement of loss has already been discussed and was given as the parameter $\alpha$ and $N_G$ in the previous discussion. To be explicitly clear $N_G$ can be found via comparison of $L_{virtual}$ and $L_{real}$ via Equation 5. (If the object being tested is a waveguide then $N_G$ represents the group index. If the object being tested is a cavity filled with a material substance that is not a waveguide then $N_G$ represents the index of the material. This is a form of spectroscopy since different materials exhibit different spectral index properties.) Note that both $\alpha$ and $N_G$ are functions of wavelength.

The following description shows that since Interference patterns produced by Virtual Reference Interferometers are equivalent to those produced by physically referenced interferometers the techniques already developed for physically referenced interferometers for measuring properties such as Chromatic Dispersion, Polarization Mode Dispersion and Polarization Dependent Loss are applicable to Virtual Reference Interferometers as well.

Dispersion

As is done in standard Interferometric Dispersion measurements the Dispersion Parameter 'D' can be measured by examining the phase of the envelope of the interference pattern, $I_{virtual}$ generated by a Virtual Reference Interferometer. FIG. 9 shows a sample interfernce pattern that has been balanced at a given wavelength. From FIG. 9 the dispersion parameter D can be extracted from the phase of the envelope (slowly varying amplitude modulation) of this interference pattern in the following way.

The Virtually referenced interference pattern contains a sinusoid with frequency $$\varphi_{envelope} = m(\beta L_{real} - k_0 L_{virtual}) = m(n_{eff} k_0 L_{real} - k_0 L_{virtual})$$

Where m depends on the type of interferometer used. This frequency is what generates the envelope of the interference pattern and it is this envelope that will be used to determine the dispersion.

Taylor expansion of $n_{eff}$ about the balanced wavelength ($\lambda_0$ in FIG. 5) and choosing m=1 gives:

$$n_{eff}(\lambda) = neff(\lambda_0) + (\lambda - \lambda_0)\frac{(dn_{eff}(\lambda_0))}{(d\lambda)} + (\lambda - \lambda_0)^2\frac{(d^2 n_{eff}(\lambda_0))}{(d\lambda)} + \ldots$$

Substitution into the phase relation gives:

$$\varphi_{envelope}(\lambda) = 2\pi\left(\frac{1}{\lambda}\left(n_{eff}(\lambda_0) - \lambda_0\frac{(dn_{eff}(\lambda_0))}{(d\lambda)}\right)L_{real} - L_{virtual}\right) + \quad \text{Eq. 7}$$

$$L_{real}\frac{(dn_{eff}(\lambda_0))}{(d\lambda)} + L_{real}\frac{(\lambda - \lambda_0)^2}{(2!\lambda)}\frac{(d^2 n_{eff}(\lambda_0))}{(d\lambda^2)} -$$

$$L_{real}\frac{(\lambda - \lambda_0)^3}{(3!\lambda)}\frac{(d^3 n_{eff}(\lambda_0))}{(d\lambda^3)} + \ldots$$

The first term in Eq. 7 (round brackets) dissapears when $L_{virtual} = N_G L_{real}$ and the phase expression is $$\varphi_{envelope}(\lambda) = 2\pi L_{real}$$

$$\left(\frac{(dn_{eff}(\lambda_0))}{(d\lambda)} + \frac{(\lambda - \lambda_0)^2}{(2!\lambda)}\frac{(d^2 n_{eff}(\lambda_0))}{(d\lambda^2)} + \frac{(\lambda - \lambda_0)^3}{(3!\lambda)}\frac{(d^3 n_{eff}(\lambda_0))}{(d\lambda^3)} + \ldots\right)$$

Taking the difference between the phases at two separate wavelengths; $\lambda_1$ and $\lambda_2$ in FIG. 5 results in:

$$\Delta\varphi_{envelope}(\lambda) = 2\pi L_{real}\left(\left(\frac{(\lambda_2 - \lambda_0)^2}{(2!\lambda_2)} - \frac{(\lambda_1 - \lambda_0)^2}{(2!\lambda_1)}\right)\frac{(d^2 n_{eff}(\lambda_0))}{(d\lambda^2)} + \right.$$

$$\left.\left(\frac{(\lambda_2 - \lambda_0)^3}{(3!\lambda_2)} - \frac{(\lambda_1 - \lambda_0)^3}{(3!\lambda_1)}\right)\frac{(d^3 n_{eff}(\lambda_0))}{(d\lambda^3)} + \ldots\right) \ldots = b\pi$$

Where b is the number of fringes between the two wavelengths. (Note that if the interference pattern has been compressed then the right side of the equation will be divided by the compression factor) Taking this phase difference again using a different pair of trough points (i.e. $\lambda_3$ and $\lambda_4$ in FIG. 5 results in a system of equations in which $$\frac{(d^2 n_{eff}(\lambda_0))}{(d\lambda^2)} \text{ and } \frac{(d^3 n_{eff}(\lambda_0))}{(d\lambda^3)}$$

can be solved directly.

The dispersion parameter can then be calculated as:

$$D(\lambda_0) = \frac{-\lambda_0}{c}\frac{(d^2(n_{eff}(\lambda_0)))}{(d\lambda^2)}$$

Other metrics of dispersion (for example but not limited to Third Order Dispersion, Group Velocity Dispersion) can be calculated from $$\frac{(d^2 n_{eff}(\lambda_0))}{(d\lambda^2)} \text{ and } \frac{(d^3 n_{eff}(\lambda_0))}{(d\lambda^3)}.$$

Differential Group Delay, Polarization Mode Dispersion and Polarization Dependent Loss One can measure the differential group delay by variation of the polarization of the input light and measuring $N_G$ for each polarization. The Polarization Mode Dispersion is the same as the Differential Group Delay for short length waveguides/fibers which is what is measured using this technology. The polarization dependent loss can be measured by variation of the polarization of the input light and measuring $\alpha$ for each polarization.

2. Tomography and Profilometry Applications (I.E. Optical Coherence Tomography, Surface profiling & Imaging)

There are several methods of using Virtual referencing in Tomography and Profilometry Applications (i.e. Optical Coherence Tomography). Two of these methods will be discussed below.

Method 1: Single Surface—Ie. Profilometry

If we would like to know the distance to a surface we can simply use the generated interference pattern and our choice of $L_{virtual}$ to determine $L_{real}$ (the distance from the first reflection to the second reflection which comes from the surface). This is a straightforward application the mathematics, which have already been discussed in examples 1 to 3. The mathematical proof of surface profilometry is the same as that given in sample application #3—Lidar and Radar Rangefinding (see below).

Method 2: Surface with Multiple Layers (I.E. Semitransparent)—I.E. Tomography

If an object is semitransparent (i.e. Biological tissue) then it will have multiple reflections from each layer within that object. This can be seen as a cascaded system as discussed in example 4. Therefore we can select the desired layer by simply choosing an appropriate length for the virtual referencing arm and selecting an appropriate wavelength range (determines how far the light will penetrate into the surface). This is very useful in Optical Coherence Tomography since it does not require a physically referenced interferometer and the information from multiple layers can be extracted at all at once from a single scan. An example of a possible physical embodiment of this system is shown in FIG. 10(a) in which a fiber with a lens (can be produced by fusing the tip of the fiber, for example in a fusion splicer) generates the first reflection and the second (and higher) reflection(s) comes from the sample.

Mathematical Proof of Virtual Reference Profilometry/Tomography

Figure 12:
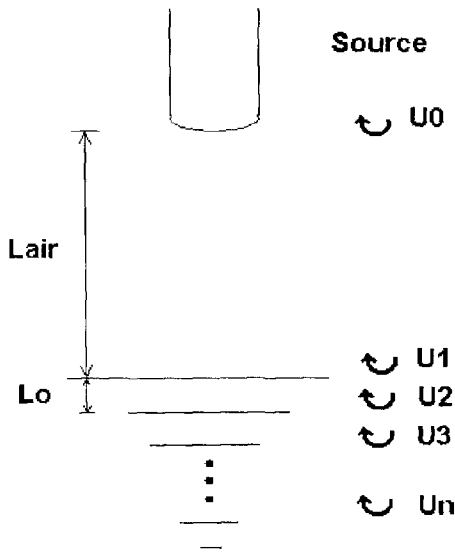
FIG. 12 illustrates proof of tomographic capability of Virtual Reference Interferometry.

This section provides the mathematical proof of Virtual Reference Profilometry/Tomography and describes the benefits of this new technology. Examples of potential Tomographic applications are ultrasound devices for medical imaging, Optical Coherence Tomography (applications) and other depth imaging applications. FIG. 12 shows a source (EM, light, sound etc) directed at a surface with multiple layers.

Each layer has a reflection point $U_n$ where n is the number of the reflection from the surface. $L_{air}$ is the distance between the source and the surface and $L_0$ is the distance between the layers. We will assume, for simplicity, that the layers are equally spaced and that the medium between the source and surface is free space, represented by ko which is the propagation constant of free space. This is not, however, necessary for the method to work.

$U_0$ is the first reflection that occurs at the interface between the source and the medium separating the source and the surface being measured. The other reflections can be described as:

$$U_1 = U_0 \alpha_1 e^{(2jk_0L_{air})}$$

$$U_2 = U_0 \alpha_2 e^{(2jk_0L_{air}+2j\beta L_0)}$$

$$U_3 = U_0 \alpha_3 e^{(2k_0L_{air}+2j\beta(2L_0))}$$

$$U_n = U_0 \alpha_n e^{(2jk_0L_{air}+2j\beta(n-1)L_0)}$$

The inteference pattern generated by the reflections is therefore:

$$I = (|(U_0 + U_1 + U_2 + U_3 + \ldots + U_n)|)^2$$

$$I = (U_0)^2 \left( \left| 1 + e^{(2jk_0L_{air})} \sum_0^M \alpha_n e^{(2j\beta(n-1)L_0)} \right| \right)^2$$

$$I = (U_0)^2$$

$$\left( \left( 1 + e^{(2jk_0L_{air})} \sum_0^M \alpha_n e^{(2j\beta(n-1)L_0)} + e^{(-2jk_0L_{air})} \sum_0^M \alpha_n e^{(-2j\beta(n-1)L_0)} \right) + \right.$$

$$\left. (U_0)^2 \left( \sum_0^M \alpha_n e^{(2j\beta(n-1)L_0)} \right) \left( \sum_0^M \alpha_m e^{(-2j\beta(m-1)L_0)} \right) \right)$$

The second term is second order small since is the multiplication of $\alpha_n \alpha_m$ and can be neglected. The interference pattern can therefore be described as:

$$I =$$

$$(U_0)^2 \left( \left( 1 + e^{(2jk_0L_{air})} \sum_0^M \alpha_n e^{(2j\beta(n-1)L_0)} + e^{(-2jk_0L_{air})} \sum_0^M \alpha_n e^{(-2j\beta(n-1)L_0)} \right) \right)$$

$$I = (U_0)^2 \left( 1 + \sum_o^M 2\alpha_n \cos(2(k_0L_{air} + \beta(n-1)L_0)) \right)$$

Filtering out the DC term gives:

$$I = 2(U_0)^2 \left( \sum_o^M \alpha_n \cos(2(k_0L_{air} + \beta(n-1)L_0)) \right)$$

If, for example, we apply virtual referencing by multiplication to this sum we will get:

$$I_{virtual} =$$

$$2(U_0)^2 \left( \sum_o^M \alpha_n \cos(2(k_0L_{air} + \beta(n-1)L_0)) \right) * \cos(2(k_0L_{air} + k_0(n-1)L_0))$$

If we then filter out the higher frequency components that are generated we get:

$$I_{virtual} = (U_0)^2 \left( \sum_o^M \alpha_n \cos(2(k_0(n-1)L_0(n_{eff}-1))) \right)$$

Where $n_{eff}$ is the index of the surface. The phase term can be used to extract the depth information of the layer and the amplitude term provides information about the reflected power from each layer. The depth and amplitude information can then be used to form an image of the surface layers.

Resolution

We now look to prove that the resolution of this technique can be made to be very high. We will assume a surface with only two reflection points for simplicity. The 'resolution' is determined by how closely the two reflected points can be while maintaining the ability to discrimite between them. The closer the two reflection points can be the higher the resolution. We will designate the separation between the two points as Δ. In this case $I_{virtual}$ has only two non zero α terms and can be described as:

$$I_{virtual} = U_0^2(\alpha_1 \cos(2k_0(n_{eff}-1)l) + \alpha_2 \cos(2k_0(n_{eff}-1)(l+\Delta)))$$

For simplicity assume that $\alpha_1 = \alpha_2$ (or even just approximately equal in magnitude) which gives:

$$I_{virtual} = \alpha U_0^2 (\cos(2k_0(n_{eff}-1)l) + \cos(2k_0(n_{eff}-1)(l+\Delta)))$$

Filtering out the high frequency components gives $$I_{virtual} = \alpha U_0^2 (\cos(2ko(n_{eff}-1)\Delta))$$

We can see from this equation that as the resolution is increased ($\Delta$ is reduced) the bandwidth required is increased. There is one very important advantage offered by virtual referencing and that is the Dynamic Bandwidth Advantage. Therefore if we use the Dynamic Bandwidth Advantage we can measure with high resolution AND reduce the required bandwidth. This is a very useful aspect of Virtual Reference Tomography. The Dynamic Bandwidth Advantage can be realized by continuously squaring and filtering out the high frequency component. The result is that:

$$I_{virtual}^n = \frac{(\alpha U_0^2)^n}{2^{n-1}} (\cos(n(2ko(n_{eff}-1)\Delta)))$$

3. Lidar and Radar Range Finding

If the medium between the two paths U0 and U1 is known then $I_{virtual}$ produces an interference is pattern that directly gives the difference between $L_{real}$ and $L_{virtual}$. Also since $L_{virtual}$ is arbitrary it can be used to determine $L_{real}$. This is very useful in Lidar and Radar Rangefinding applications since it does not require a physically referenced interferometer. An example of the physical embodiments of this system is shown in FIG. 10(b). The surface of the target determines $L_{real}$.

In the sample embodiment shown in FIG. 10(b)

$$I_{real} = [U0 + \alpha U0 e^{(2jkoL_{real})}]^2 = U0^2(1+\alpha^2+2\alpha\cos(2koL_{real})) = I_0 + I_1 \cos(2koL_{real})$$

After operation (say we choose multiplication) by a given sinusoid $$I_{virtual} = I_{real} \cos(2koL_{virtual})$$

$$I_{virtual} = I_0 \cos(2koL_{virtual}) + \frac{I_1}{2}(\cos(2(koL_{real}+koL_{virtual}))\cos(2(koL_{real}-koL_{virtual})))$$

The phase of the envelope in this case is:

$$\varphi_{envelope} = 2ko(L_{real}-L_{virtual}) = 4\frac{\pi}{\lambda}(L_{real}-L_{virtual})$$

The phase difference between two peaks or troughs in the interference pattern can be expressed as $$\Delta\varphi_{envelope} = 2ko(L_{real}-L_{virtual}) = 4\pi(L_{real}-L_{virtual})\left(\frac{1}{\lambda_1}-\frac{1}{\lambda_2}\right) = b\pi$$

Where $\lambda_1$ and $\pi_2$ are the wavelength locations of two peaks or troughs in the envelope of the interference pattern $I_{virtual}$ and b is the number of troughs or peaks between these two wavelengths. Note that $L_{virtual}$ can be chosen such that it is close to the expected value of $L_{real}$ to reduce bandwidth requirements.

The distance can then be calculated as $$L_{real} = L_{virtual} + \frac{b}{4}\left(\frac{(\lambda_1\lambda_2)}{(\lambda_2-\lambda_1)}\right)$$

4. Thermal Sensing

Since the virtual path does not change with temperature this makes it a very useful reference. Changes in temperature will show up as changes in length of the test path $L_{real}$ or changes in the properties of the waveguide (optical fiber). As a result the mathematics are the same as previously described only we must replace $L_{real}$ with $L_{real}$ at a specific temperature). This makes the system a very useful as a thermometer/temperature sensor and is ideal for space borne applications.

5. Tension and Stress Sensing

Since the virtual path does not change with stress this makes it a very useful reference since changes in tension or stress will show up as changes in length for the real path $L_{real}$. This makes the system a very useful for measuring tension or stress. As a result the mathematics are the same as previously described only we must replace $L_{real}$ with $L_{real}$ (stress or strain). This makes virtually balanced interferometers ideal for civil engineering based applications such as monitoring the tension in a building or a bridge and other related uses.

Note that one can also measure the changes in the properties of the waveguide or fiber under stress and use this to infer the magnitude of the stress. For example a fiber under stress may have changes in its dispersion properties that can be measured and used to infer stress/strain.

6 & 7. Ultrasound, Sonography and Sonar

As noted previously a Virtual Reference Interferometer is useful for applications involving waves in general. Sound is a type of longitudinal wave that experiences interference and as such there are virtual referencing applications for sound as well.

Figure 11A:
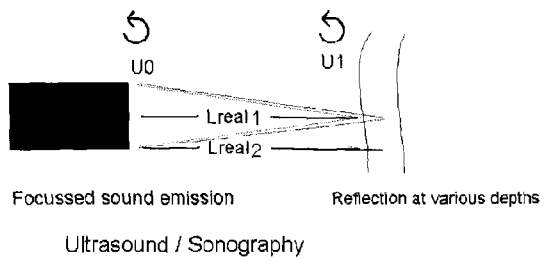
FIG. 11 illustrates sample physical embodiments of Ultrasound Sonography/Tomography and Sonar (Rangefinding) applications of Virtual Reference (Balanced) Interferometers.
Figure 11B:
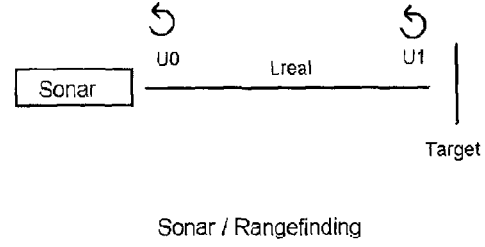

If the medium between the two paths U0 and U1 is known then the propagation constant $\beta$ of sound in a medium is well known and $I_{virtual}$ produces an interference pattern that directly gives the difference between $L_{real}$ and $L_{virtual}$. Since $L_{virtual}$ is arbitrary it can be used to determine $L_{real}$. This is very useful in Ultrasound, Sonography and Sonar applications as it does not require a physical interferometer. An example of the physical embodyments of these systems is shown in FIGS. 11(a) and 11(b). For Ultrasound and Sonography the wavelength of the sound is usually small and determines the depth of penetration into a surface (determines $L_{real}$). For Sonar Rangefinding the wavelengths of sound can vary and the surface of the target determines $L_{real}$.

In the sample embodyments shown in FIG. 11 the real interference pattern produced is $$I_{real} = [U0 + \alpha U0 e^{(2i\beta_{sound}L_{real})}]^2 = U0^2(1+\alpha^2+2\alpha\alpha co (2\beta_{sound}L_{real})) + I_0 + I_1 \cos(2\beta_{sound}L_{real})$$

After operation (multiplication) by a given sinusoid $$I_{virtual} = I_{real} \cos(2\beta_{sound}L_{virtual})$$

$$I_{virtual} = I_0 \cos(2\beta_{sound}L_{virtual}) + \frac{I_1}{2}(\cos(2(\beta_{sound}L_{real}+\beta_{sound}L_{virtual}))\cos(2(\beta_{sound}L_{real}-\beta_{sound}L_{virtual})))$$

The phase of the envelope in this case is:

$$\phi_{envelope} = 2\beta_{sound}(L_{real}-L_{virtual})$$

The phase difference between two peaks or troughs in the interference pattern can be expressed as $$\Delta\phi_{envelope}=2\beta_{sound}(L_{real}-L_{virtual})=b\pi$$

Once again the phase of the envelope is related to the separation between the paths and can therefore be used to determine the real distance $L_{real}$ in the same way as previously discussed.

Note that the proof in the section on Tomography and Profilometry applications is applicable to sound waves as well.

8. Anywhere there is Interference

The above examples are not meant to be exhaustive only to illustrate to vast applicability of this new invention to multiple fields of use. The technology is applicable generally wherever there is interference.

The invention claimed is:

1. An interferometer system for generating a virtually referenced interference pattern, the system characterized by:
   a) a wave generating source operable to emit a wave through one or more test paths;
   b) an interferometer with one or more test paths;
   c) a detector for measuring a physical spectral interference pattern produced;
   d) a processor for modulating and analyzing the physical spectral interference pattern produced in the interferometer;
   wherein the physical spectral interference pattern produced in the interferometer is mixed with a simulated virtual reference spectral interference pattern via an operation in the spectral domain;
   wherein the result of such operation results in a spectral interference pattern with a high frequency component and a low frequency component;
   wherein the low frequency component contains information about the difference between the properties of the one or more test paths and the simulated virtual reference pattern;
   wherein the simulated virtual reference pattern balances the group delay in the interferometer at a given wavelength such that the low frequency component is equivalent to that which would be produced by physically balancing the group delay in the interferometer at that wavelength.

2. The system of claim 1, characterized in that the one or more test paths are each adapted to be provided with a test waveguide and the system is operable to characterize the dispersion properties of the test waveguide.

3. The system of claim 1, characterized in that the operation in the spectral domain comprises one or more of addition, subtraction, multiplication or any combination or exponentiation thereof of the simulated virtual reference spectral interference pattern with the physical spectral interference pattern produced by the interferometer, resulting in a spectral interference pattern in the spectral domain with a low frequency component that contains information regarding the differences between the one or more test paths and virtual reference paths.

4. The system of claim 1, characterized in that the operation equivalently adds the spectral content of the simulated virtual reference spectral interference pattern to the spectral content of the physical spectral interference pattern directly in the Fourier Domain via convolution of the Fourier Transform of each spectral interference pattern in the Fourier Domain followed by an inverse Fourier transform of the result to yield an amplitude modulated spectral interference pattern.

5. The system of claim 1, characterized in that the interferometer is selected from the group comprising: a Fabry-Perot; a Michelson; a Mach Zehnder; and an unreferenced single arm.

6. A method of generating an interference pattern of two or more waves, characterized in that the method comprises the steps of:
   (a) generating a physical spectral interference pattern by operation of a physically unreferenced or unbalanced interferometer, wherein the interferometer has one or more test paths;
   (b) generating a virtual reference spectral interference pattern; and
   (c) generating a spectral interference pattern via an operation that combines the spectral interference patterns generated in (a) and (b) directly in the spectral domain, resulting in a spectral interference pattern with a high frequency component and a low frequency component;
   (d) extracting the differences between the properties of the one or more test paths and a virtual reference path from the low frequency component in (c).

7. The system of claim 1, characterized in that the wave generating source is selected from the group comprising: a tunable laser; and a broadband source.

8. The system of claim 1, characterized in that the detector is selected from the group comprising: a photodetector; and a spectrum analyzer.

* * * * *